United States Patent [19]

Preiner et al.

[11] Patent Number: 4,515,976

[45] Date of Patent: May 7, 1985

[54] METHOD FOR PREPARING ASYMMETRICAL DISILOXANES

[75] Inventors: Gerhard Preiner; Johann Müller, both of Burghausen, Fed. Rep. of Germany

[73] Assignee: Wacker-Chemie GmbH, Munich, Fed. Rep. of Germany

[21] Appl. No.: 578,389

[22] Filed: Feb. 8, 1984

[30] Foreign Application Priority Data

Apr. 8, 1983 [DE] Fed. Rep. of Germany ....... 3312737

[51] Int. Cl.$^3$ ................................................ C07F 7/08
[52] U.S. Cl. .................................................... 556/453
[58] Field of Search ........................................ 556/453

[56] References Cited

U.S. PATENT DOCUMENTS 2,483,963 10/1949 Barry et al. ...................... 556/453 X
3,595,896 7/1971 Nitzsche et al. ................. 556/453 X

*Primary Examiner*—Paul F. Shaver

[57] ABSTRACT

Asymmetrical disiloxanes are prepared by reacting (a) a silane containing three SiC-bonded monovalent organic radicals in which at least one may be substituted with Si-bonded hydrogen and an SiOC-bonded monovalent organic radical with (b) a symmetrical disiloxane which is different from the disiloxane obtained from the hydrolysis of silane (a), and contains at least two identical substituents in the presence of water and an acid at a temperature of from −10° to about 50° C.

8 Claims, No Drawings

METHOD FOR PREPARING ASYMMETRICAL DISILOXANES

The present invention relates to a method for preparing disiloxanes and more particularly to a method for preparing asymmetrical disiloxanes.

BACKGROUND OF THE INVENTION

In the preparation of asymmetrical disiloxanes by the cohydrolysis of, for example, trimethylchlorosilane and dimethylchlorosilane, it is impossible to produce asymmetrical disiloxanes in any quantity which substantially exceeds the amount of available symmetrical disiloxane. (See Journal fur Praktische Chemie, Vol. 11, 1960, pp. 336–340).

German Patent Application No. 30 02 683 (published Aug. 7, 1980, Inventor: N. N. Novichy) describes a method for preparing pentamethyldisiloxane by reacting trimethylsilane with dimethylchlorosilane at a low temperature in the presence of pyridine. The use of pyridine in large scale production creates problems, particularly since it is toxic and presents a health hazard. In addition, the expense of recovering the pyridine from the resultant product makes the process very unattractive on a commercial scale.

Therefore, it is an object of the present invention to provide a method for preparing asymmetrical disiloxanes. Another object of the present invention is to provide a method for preparing improved yields of asymmetrical disiloxanes. A further object of the present invention is to provide a method for preparing asymmetrical disiloxanes in the absence of pyridine.

SUMMARY OF THE INVENTION

The foregoing objects and others which will become apparent from the following description are accomplished in accordance with this invention, generally speaking, by providing a method for preparing asymmetrical disiloxanes which comprises reacting (a) a silane containing three Si-bonded monovalent organic radicals of which at least one may be substituted with Si-bonded hydrogen and an SiOC-bonded monovalent organic radical with (b) a symmetrical disiloxane which is different from the disiloxane obtained from the hydrolysis of silane (a) and contains at least two identical substituents in the presence of water and an acid.

DESCRIPTION OF THE INVENTION

In accordance with the method of this invention, a silane (a) of the formula $$R_3SiOR^1,$$

where the R radicals, which may be the same or different, represent hydrogen or monovalent SiC-bonded organic radicals and $R^1$ represents an SiOC-bonded monovalent organic radical, is reacted with a symmetrical disiloxane of the formula $$R_n'R_{3-n}SiOSiR_{3-n}R',$$

where R is the same as above, R' may be the same as R, but differs from R, and n is 1, 2 or 3, preferably 1, in the presence of water and an acid. The symmetrical disiloxane (b) is prepared prior to the addition of the silane (a).

Preferred examples of organic radicals represented by R and R' are alkyl radicals having from 1 to 3 carbon atoms per radical, such as the methyl, ethyl and n-propyl radical, alkenyl radicals having from 1 to 3 carbon atoms per radical, such as the vinyl and the allyl radical, and substituted hydrocarbon radicals having from 1 to 6 carbon atoms per radical, such as the chloromethyl, gamma-chloropropyl and the gamma-methacryloxypropyl radical.

It is preferred that $R^1$, which represents an SiOC-bonded monovalent organic radical, consist of carbon, hydrogen and optionally oxygen. Preferred examples of $R^1$ are methyl, ethyl, propyl, isopropyl, tert-butyl and the methoxyethylene radical, as well as the acetyl radical.

In accordance with a preferred embodiment of this invention, the silane (a) is a silane of the formula $$(CH_3)_3SiOR^1,$$

wherein $R^1$ is the same as above, and the disiloxane (b) is a tetramethyldisiloxane, i.e., a disiloxane of the formula $$H(CH_3)_2SiOSi(CH_3)_2H.$$

An example of an asymmetrical disiloxane obtained from the method of this invention is pentamethyldisiloxane, i.e., a disiloxane of the formula $$(CH_3)_3SiOSi(CH_3)_2H.$$

Another example of silicon-containing reactants which may be employed in the method of this invention is the reaction of vinyldimethylethoxysilane with hexamethyldisiloxane in the presence of acid and water.

Simple experiments will determine whether it is better to use allyldimethoxysilane and hexamethyldisiloxane as silicon-containing reactants, or whether trimethylethoxysilane and 1, 3-diallyl-1,1,3,3-tetramethyldisiloxane should be used.

Preferably the molar ratio of the silane (a), i.e., trimethylethoxysilane, to the disiloxane (b), i.e., the tetramethyldisiloxane, is in the range of from 2:1 to 4:1. If the molar ratio of the silane (a) to the disiloxane (b) is smaller than 2:1, optimal yields cannot be obtained. An increase in molar ratio of the silane (a) to the disiloxane (b) does not produce any additional advantages.

The amount of water is preferably between about 0.5 to about 1.5 moles per mole of silane (a). If the molar ratio of water to the silane (a) is less than about 0.5:1, the yields are no longer optimal. Molar ratios of water to silane (a) greater than 1.5:1 do not yield any additional advantages.

It is preferred that the acid employed in the method of this invention be a protonic acid having a negative logarithm of the acid constant of no more than 1 ($pK_s$ or $pK_a$, see H. R. Christen, "Grundlagen der allgemeinen und anorganischen Chemie", Frankfurt/Main, 1973, page 354). Examples of such acids are hydrochloric acid, sulfuric acid and phosphoric acid, with hydrochloric acid being the preferred acid because in the presence of water it has only a slight equilibrating effect and because it is readily available.

The acid is preferably used in an amount of from 0.01 to 2 percent by weight and more preferably from about 0.1 to 1 percent by weight, based on the total weight of the silane, disiloxane, water and acid.

Preferably the method of this invention is carried out at temperatures between −10° C. and 50° C., and more preferably between 0° and 25° C. in order to prevent equilibration.

Furthermore, it is preferred that the process of this invention be performed in stages and that the silane (a) be added to a mixture containing water, disiloxane (b) and acid.

Also, it is preferred that the acid be neutralized by the addition of, for example, sodium bicarbonate as soon as the reaction is completed. The mixture can then be washed with water and the disiloxane can be dried and purified by distillation.

The method of this invention can provide yields of the order of from 80 to 95 percent by weight based on theoretical.

EXAMPLE

To a mixture having an initial temperature of 0° C. and consisting of 1340 gm (10 mole) of tetramethyldisiloxane, 220 gm of 1N HCl and 140 gm of water, i.e., containing 0.47 percent by weight of HCl, are added dropwise, 2360 gm (20 mole) of trimethylethoxysilane and at a rate such that the temperature does not exceed 5° C. As soon as the addition of the trimethylethoxysilane is complete, the acid is neutralized by the addition of 40 gm of sodium bicarbonate. The resultant mixture is then washed 5 times with 500 gm of water each and dried with sodium sulfate. According to the $^1$H-NMR spectrum, the mixture consists of 90 mole percent of pentamethyldisiloxane and 10 mole percent of hexamethyldisiloxane. The resultant product is distilled in a packed column and 2350 gm of pentamethyldisiloxane is recovered (80 percent by weight of theoretical).

What is claimed is:

1. A method for preparing asymmetrical disiloxanes which comprises reacting (a) a silane having three SiC-bonded monovalent organic radicals of which at least one may be substituted with Si-bonded hydrogen and an SiOC-bonded monovalent organic radical with (b) a symmetrical disiloxane which is different from the disiloxane obtained from the hydrolysis of silane (a) in which at least two of the substituents of disiloxane (b) are the same in the presence of water and an acid.

2. The method of claim 1, wherein silane (a) is represented by the formula $(CH_3)_3SiOR^1$, wherein $R^1$ is a monovalent organic radical consisting of carbon and hydrogen and disiloxane (b) is tetramethyldisiloxane.

3. The method of claim 1, wherein silane (a) is represented by the formula $(CH_3)_3SiOR^1$, wherein $R^1$ is a monovalent organic radical consisting of carbon, hydrogen and oxygen and disiloxane (b) is tetramethyldisiloxane.

4. The method of claim 1, wherein the molar ratio of silane (a) to disiloxane (b) is from 2:1 to 4:1.

5. The method of claim 1, wherein the acid is a protonic acid having a $pK_s$-value which does not exceed 1.

6. The method of claim 5, wherein the protonic acid is hydrogen chloride.

7. The method of claim 1, wherein the reaction is conducted at a temperature of from −10° C. to 50° C.

8. The method of claim 1, wherein silane (a) is added to a mixture consisting of disiloxane (b), water and acid.

* * * * *